United States Patent
Lu

(10) Patent No.: US 10,206,626 B2
(45) Date of Patent: Feb. 19, 2019

(54) BIOSIGNAL MEASUREMENT AND TRANSMISSION APPARATUS HAVING SIMPLIFIED SIGNAL SLOT

(71) Applicant: Chuen Wei Lu, Taoyuan (TW)

(72) Inventor: Chuen Wei Lu, Taoyuan (TW)

(*) Notice: Subject to any disclaimer, the term of this patent is extended or adjusted under 35 U.S.C. 154(b) by 859 days.

(21) Appl. No.: 14/802,935

(22) Filed: Jul. 17, 2015

(65) Prior Publication Data

US 2016/0030125 A1 Feb. 4, 2016

(30) Foreign Application Priority Data

Jul. 31, 2014 (TW) .............................. 103213604 U

(51) Int. Cl.
*G06F 13/20* (2006.01)
*G06F 13/40* (2006.01)
(Continued)

(52) U.S. Cl.
CPC ............... *A61B 5/72* (2013.01); *A61B 5/742* (2013.01); *G06F 13/20* (2013.01);
(Continued)

(58) Field of Classification Search
CPC ..... G06F 13/20; G06F 13/4063; A61B 19/44; A61B 5/02055; A61B 5/14532;
(Continued)

(56) References Cited

U.S. PATENT DOCUMENTS 5,193,547 A * 3/1993 Evans, II ............... A61B 5/021
600/481
6,381,484 B1 * 4/2002 Ayanruoh ............... A61B 5/00
600/407
(Continued)

*Primary Examiner* — Glenn A. Auve
(74) *Attorney, Agent, or Firm* — Huffman Law Group, PC

(57) ABSTRACT

A biosignal measurement and transmission apparatus having a simplified signal slot as provided is configurable for receiving signals from a biosignal detection apparatus and a biosignal detection correction unit and for performing signal transfer and analysis operations. The measurement and transmission apparatus includes: a housing including a single detection slot, which is used for receiving signals from the biosignal detection apparatus and the biosignal detection correction unit, wherein a connector of the biosignal detection apparatus and a connector of the biosignal detection correction unit share the detection slot; a detection slot inserted apparatus determining unit, connected to a wire of the detection slot, used for receiving a signal from the detection slot, and is configurable for identifying the type of an inserted apparatus, wherein the detection slot inserted apparatus determining unit identifies the type of an apparatus by making a judgment according to a signal input pin of the inserted apparatus; or an apparatus code is appended to an output signal of the inserted apparatus, so that the detection slot inserted apparatus determining unit can determine, according to the apparatus code, what kind of physiological detection device the inserted apparatus belongs to, or determine a control group unit thereof. When the wireless signal transmission unit is of an external type, the wireless signal transmission unit also uses the detection slot, and the detection slot inserted apparatus determining unit uses the same logic to determine various inserted apparatuses.

12 Claims, 6 Drawing Sheets

(51) Int. Cl.
  *A61B 5/00* (2006.01)
  *A61B 5/145* (2006.01)
  *A61B 5/021* (2006.01)
  *A61B 5/024* (2006.01)
  *A61B 5/01* (2006.01)

(52) U.S. Cl.
  CPC ........ G06F 13/4063 (2013.01); *A61B 5/0022* (2013.01); *A61B 5/01* (2013.01); *A61B 5/021* (2013.01); *A61B 5/024* (2013.01); *A61B 5/14532* (2013.01); *A61B 5/4872* (2013.01)

(58) Field of Classification Search
  CPC ..... A61B 5/0022; A61B 5/742; A61B 5/4872; A61B 5/72
  See application file for complete search history.

(56) References Cited

U.S. PATENT DOCUMENTS

| | | | |
|---|---|---|---|
| 2010/0225468 A1* | 9/2010 | Sievert | H04L 63/0853 340/539.12 |
| 2012/0000705 A1* | 1/2012 | Cornelius | G06F 1/266 174/84 R |
| 2014/0275844 A1* | 9/2014 | Hoseit | A61B 5/0084 600/301 |
| 2015/0042879 A1* | 2/2015 | Chiang | G09G 5/005 348/469 |
| 2016/0338590 A1* | 11/2016 | Sagalovich | A61B 5/0022 |

* cited by examiner

BIOSIGNAL MEASUREMENT AND TRANSMISSION APPARATUS HAVING SIMPLIFIED SIGNAL SLOT

BACKGROUND OF THE INVENTION

Field of the Invention

The present creation relates to a biosignal measurement and transmission apparatus, and more particularly to a biosignal measurement and transmission apparatus having a simplified signal slot.

Description of the Prior Art

With the advancement of living standards and healthcare, general life expectancy has gradually increased along the average age of the population. The ageing of the society leads to various problems in social welfare, medical and pharmaceutical technologies, and the social security system, as an increasing amount of elderly people do not receive adequate care from their families. Furthermore, the percentage of the population suffering from chronic diseases such as hypertension, diabetes, gout, hyperlipidemia and heart disease has risen sharply as lifestyle and eating habits have changed. Due to limited staffing in health facilities, patients suffering from chronic diseases such as diabetes and hypertension cannot be monitored effectively and comprehensively in the health facilities. Therefore, physiological monitoring systems for home use would not only take the place of costly medical manpower and resources in health facilities, the symptoms and health problems of patients could be further observed from data obtained through long-term continuous physiological monitoring. Therefore, physiological monitoring systems for home use can be considered to be the first line of defense for health and medical care.

Multiple biosignal measurement and transmission apparatuses are currently available in the market; they can be used to measure certain physiological parameters and transmit these parameters to a local or remote electronic apparatus, to be used for medical assessment or to assist in medical care. However, as the needed measurement function may change, the available biosignal measurement and transmission apparatuses may be provided with many slots for different functions, which affects the operating efficiency of the user because the user needs to determine the appropriate slots for insertion. Selecting a wrong slot for insertion may cause damage to the equipment and the detection apparatus. The more slots that are required, the larger the apparatus will be; as a result, the apparatus is bulky and inconvenient.

SUMMARY OF THE INVENTION

A main objective of the present creation is to provide a biosignal measurement and transmission apparatus having a simplified signal slot, which is advantageous in that signals from different types of apparatuses can be transmitted through one detection slot, and the user would not need to determine which slot a particular apparatus should be inserted; this would improve user efficiency and avoid damaging the device by selecting a wrong slot for insertion; furthermore, a reduction in the number of slots would also reduce the size and the number of parts of the device, thereby reducing costs. In the present creation, the data report can be uploaded to a remote server via a wireless network, for interpretation by a medical institution.

To achieve the above objective, the present creation provides a biosignal measurement and transmission apparatus having a simplified signal slot. The biosignal measurement and transmission apparatus having a simplified signal slot includes: a biosignal detection apparatus, the biosignal detection apparatus being used for detecting at least one biosignal of a user, wherein the biosignal detection apparatus includes a connector for transmitting a signal, and the connector includes multiple pins for signal transfer; a biosignal detection correction unit for providing data from a reference group for a biosignal detection apparatus and providing reference data to the biosignal detection apparatus to assist in the detection of the biosignal, the biosignal detection correction unit having a connector that includes multiple pins for signal transfer, wherein the biosignal detection apparatus and the biosignal detection correction unit have different signal pins, and different biosignal detection apparatuses have different pins for signal transfer; and an electronic device, including: a housing for accommodating relevant apparatuses of the present creation, and a detection slot for receiving signals from the biosignal detection apparatus and the biosignal detection correction unit, and transferring the received signals to a next-stage apparatus via a wire; wherein a connector of the biosignal detection apparatus and a connector of the biosignal detection correction unit share the detection slot, and the detection slot includes multiple pins adapted to connect to inserted pins of the biosignal detection apparatus and the biosignal detection correction unit for signal transfer;

wherein the electronic device further includes: a detection slot inserted apparatus determining unit, connected to the wire of the detection slot, used for receiving a signal from the detection slot, and is configurable for identifying the type of an inserted apparatus; a processor, connected to the detection slot inserted apparatus determining unit, used for receiving a signal from the detection slot inserted apparatus determining unit and performing relevant computation and processing, wherein a logic unit corresponding to the inserted apparatus is mounted in the processor, and the logic unit performs different logic operations depending on the types of input signals from different inserted apparatuses; and a storage unit for storing relevant data in the present creation, the storage unit having memory blocks that correspond to different inserted apparatuses, so as to separately store measurement information of the different inserted apparatuses, for subsequent display, management and use.

In order to make the present creation more comprehensible, features and effects of the present creation are described in detail below through preferred embodiments with reference to the drawings and drawing numbers.

DETAILED DESCRIPTION

Figure 1:
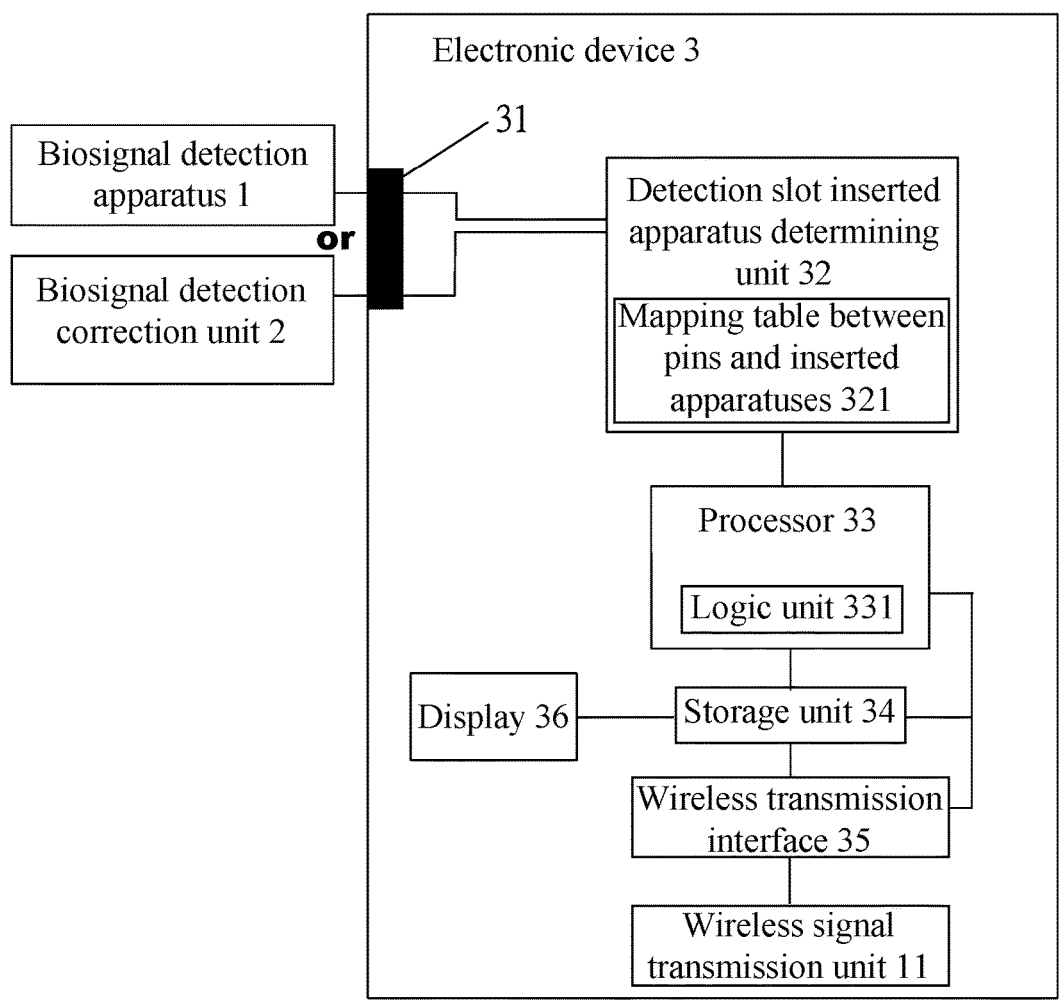
FIG. 1 is a block diagram illustrating the connection of elements in the present creation, wherein a mapping table between pins and inserted apparatuses is stored in the detection slot inserted apparatus determining unit.

Referring to FIG. 1 to FIG. 6, a biosignal measurement and transmission apparatus having a simplified signal slot according to the present creation is shown. The apparatus includes the following elements: a biosignal detection apparatus 1, a biosignal detection correction unit 2, and an electronic device 3.

The biosignal detection apparatus 1 is used for detecting at least one biosignal of a user, the biosignal including heartbeat, blood pressure, blood glucose, body fat, body temperature and the like. The biosignal detection apparatus 1 includes a connector 100 for transmitting a signal. The connector includes multiple pins 101 for signal transfer. In the present creation, the pins 101 include a ground pin, a power pin, and multiple signal pins. In the present creation, the property of the biosignal detection apparatus 1 is determined by the manner in which the pins are configured, for example, the biosignal detection apparatus 1 is a biosignal detection apparatus for detecting heartbeat or a biosignal detection apparatus for detecting blood glucose.

The biosignal detection correction unit 2 provides data of a control group for a biosignal detection apparatus 1, and provides reference data to the biosignal detection apparatus 1 to assist in detection of the biosignal. The control group unit is necessary only for some biosignals such as blood glucose, body fat and cholesterol. The biosignal detection correction unit 2 is not necessary for the measurement of biosignals such as heartbeat and blood pressure. The biosignal detection correction unit 2 has a connector 200 that includes multiple pins 201 for signal transfer.

The electronic device 3 includes: a housing 31 for accommodating relevant apparatuses of the present creation, and a detection slot 31 for receiving signals from the biosignal detection apparatus 1 and the biosignal detection correction unit 2, and transferring the received signals to a next-stage apparatus via a wire, wherein a connector 100 of the biosignal detection apparatus 1 and a connector 200 of the biosignal detection correction unit 2 share the detection slot 31. The detection slot 31 includes multiple pins adapted to connect to inserted pins of the biosignal detection apparatus 1 and the biosignal detection correction unit 2 for signal transfer.

In the present creation, the biosignal detection apparatus 1 and the biosignal detection correction unit 2 have different signal pins. Different biosignal detection apparatuses 1 also have different pins for signal transfer. For example, one slot has eight pins, wherein pins 1 and 8 serve as power pins. Pins 2, 3, 4, and 5 serve as signal pins for a first biosignal detection apparatus 1 (for example, a blood glucose monitoring machine); pins 2, 3, 4, and 6 serve as signal pins for a second biosignal detection apparatus 1 (for example, a blood pressure monitoring machine); pins 4, 5, 6, and 7 serve as signal pins for the biosignal detection correction unit 2.

In the present creation, different apparatus codes may be assigned to the biosignal detection apparatus 1 and the biosignal detection correction unit 2, and when an apparatus transfers a signal, the apparatus code of the apparatus is also transferred along with the signal. For example, the apparatus code of the biosignal detection apparatus 1 is AX1 and the apparatus code of the biosignal detection correction unit 2 is BW1; therefore, when a signal is transferred, the source of the signal can be determined according to the apparatus code.

The electronic device 3 further includes a detection slot inserted apparatus determining unit 32 is connected to the wire of the detection slot 31, used for receiving a signal from the detection slot 31, and is configurable for identifying the type of an inserted apparatus. The identification may be performed by using one of the following two methods:

(1) Making a determination according to pins from which the signal is input, automatically interpreting differences between pins of different apparatuses, and determining transmission input pins of the signal, wherein a mapping table 321 between pins and inserted apparatuses is stored in the detection slot, inserted apparatus determining unit 32, and the mapping table defines a correspondence between a signal output pin of each apparatus inserted into the detection slot 31 and the apparatus. Therefore, the detection slot inserted apparatus determining unit 32 searches, according to signal pins of an inserted apparatus, for the corresponding apparatus in the table, determines the type of the signal from the inserted apparatus, and transfers the signal to a next-stage apparatus for subsequent processing.

In the above example, it can be learned through detection that the pins from which the signal is input are the pins 2, 3, 4, and 5, and accordingly, it can be found by searching the table that the inserted apparatus is the first biosignal detection apparatus 1 (that is, the blood glucose monitoring machine); similarly, when it is learned that the pins from which the signal is input are the pins 4, 5, 6, and 7, it can be found by searching the table that the inserted apparatus is the biosignal detection correction unit 2.

(2) Making a determination according to the apparatus code, determining differences between apparatuses according to different apparatus codes, and determining the position from which the signal is transmitted, wherein an apparatus code identification table 322 is stored in the detection slot inserted apparatus determining unit 32, and the mapping table defines a correspondence between an apparatus code in an output signal of each apparatus inserted into the detection slot 31 and the apparatus. Therefore, the detection slot inserted apparatus determining unit 32 searches, according to the apparatus code of an inserted apparatus, for the corresponding apparatus in the table, and thus can determine the type of the signal of the inserted apparatus according to the correspondence between identification codes and inserted apparatuses, and transfers the signal to a next-stage apparatus for subsequent processing.

In the above example, it is learned through detection that the apparatus code of the input signal is AX1, and accordingly, it can be found by searching the table that the inserted apparatus is the first biosignal detection apparatus 1 (that is, the blood glucose monitoring machine); similarly, when it is learned that the apparatus code of the input signal is BW1, it can be found by searching the table that the inserted apparatus is the biosignal detection correction unit 2.

A processor 33 is connected to the detection slot inserted apparatus determining unit 32 and used for receiving a signal from the detection slot inserted apparatus determining unit 32 and performing relevant computation and processing, wherein a logic unit 331 corresponding to the inserted apparatus is mounted in the processor 33, and the logic unit 331 performs different logic operations depending on the types of input signals from different inserted apparatuses. For example, upon receiving measurement data related to blood glucose, the logic unit 331 automatically performs a logic operation related to blood glucose; upon receiving measurement data related to blood pressure, the logic unit 331 automatically performs a logic operation related to blood pressure; and upon receiving reference data, the logic unit 331 automatically performs an operation related to the reference data.

A storage unit 34 is used for storing relevant data in the present creation. The storage unit 34 has memory blocks that correspond to different inserted apparatuses, so as to separately store measurement information of the different inserted apparatuses, for subsequent display, management and use.

A wireless transmission interface 35, connecting the processor 33 to the storage unit 34, is used for modulating a signal from the processor 33 into a wireless signal for transfer, or is used for demodulating a wireless signal into a baseband signal for signal processing by the processor 33.

A display 36 disposed in the electronic device 3 and connected to the storage unit 22, is used for displaying relevant measurement information.

Figure 2:
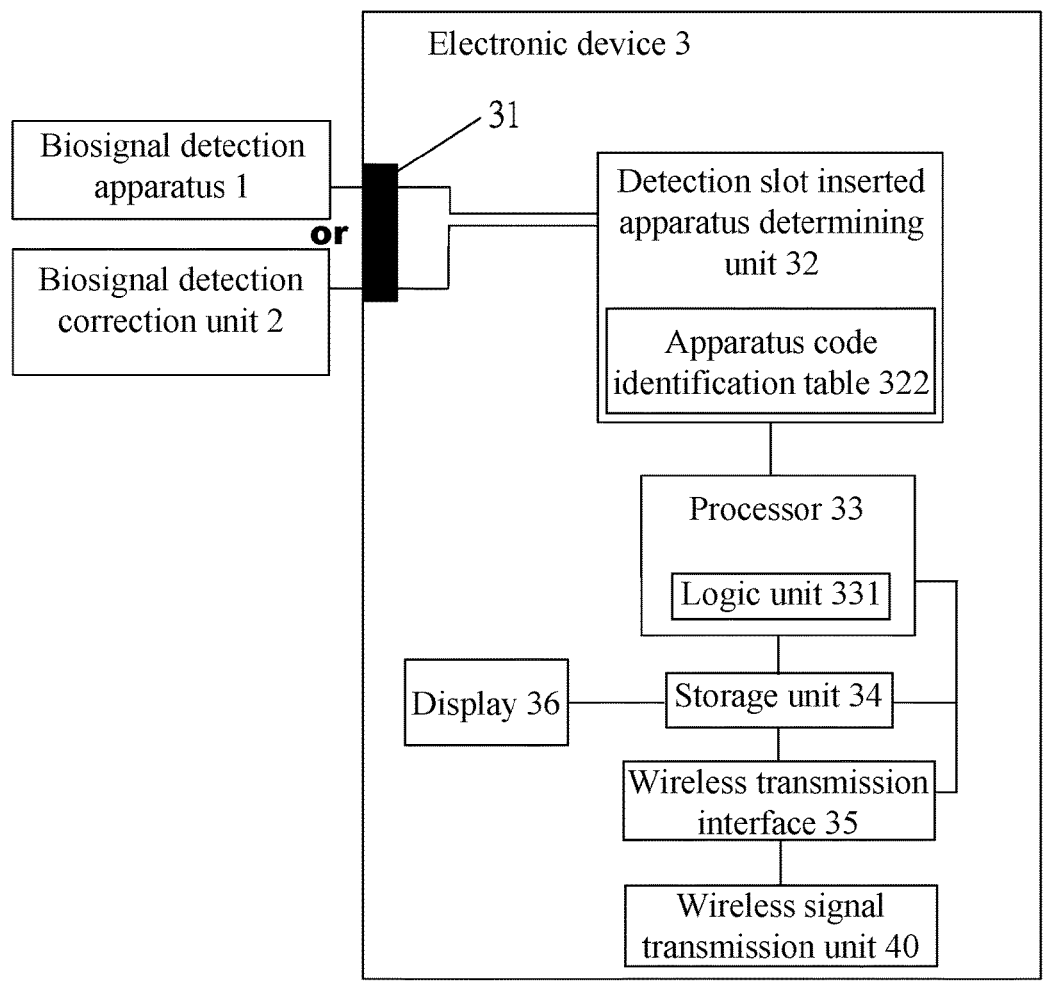
FIG. 2 is a block diagram illustrating the connection of elements in the present creation, wherein an apparatus code identification table is stored in the detection slot inserted apparatus-determining unit.

A wireless signal transmission unit 40 is connected to the wireless transmission interface 35. The wireless signal transmission unit 40 is used for transmitting a biosignal after detection. The wireless signal transmission unit 40 is mounted in the electronic device 3, as shown in FIG. 1 and FIG. 2, and transfers the detection result to another neighboring electronic apparatus such as a mobile phone or computer according to a wireless communications protocol. Preferably, in the present creation, the wireless signal transmission unit 40 is a Bluetooth transmission unit, and a transmission connector 41 of the wireless signal is a USB connector.

Figure 3:
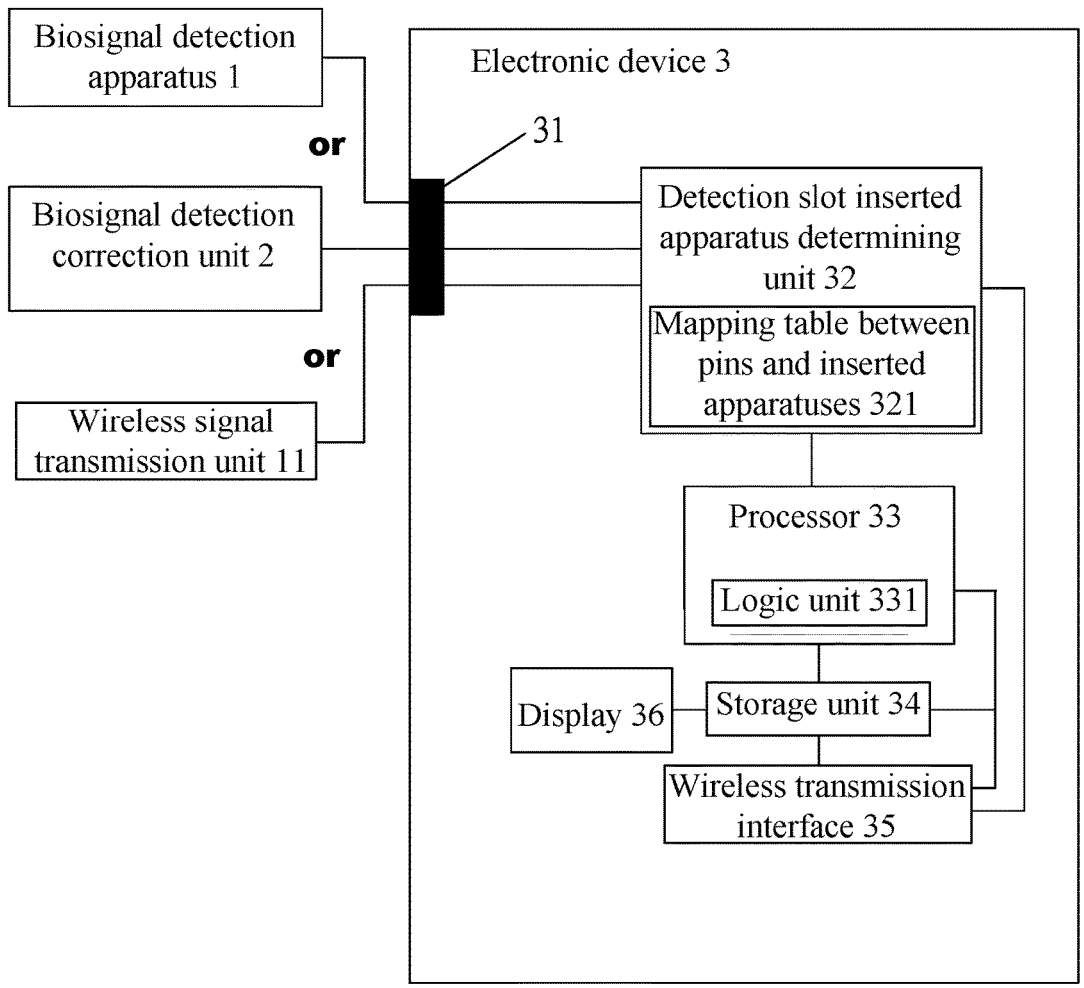
FIG. 3 is a block diagram illustrating the connection of elements in the present creation, wherein a mapping table between pins and inserted apparatuses is stored in the detection slot inserted apparatus determining unit, and a wireless signal transmission unit is externally connected to the electronic device.
Figure 4:
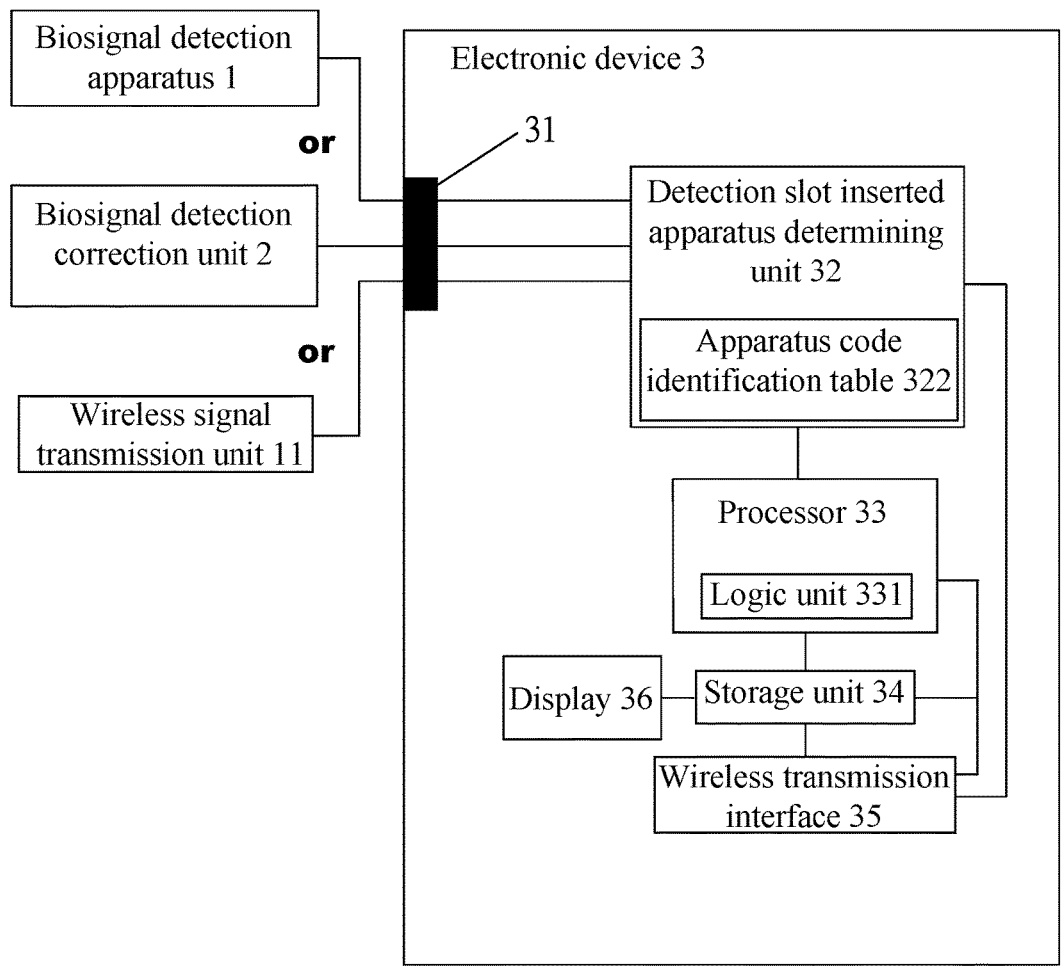
FIG. 4 is a block diagram illustrating the connection of elements in the present creation, wherein an apparatus code identification table is stored in the detection slot inserted apparatus determining unit, and a wireless signal transmission unit is externally connected to the electronic device.
Figure 5:
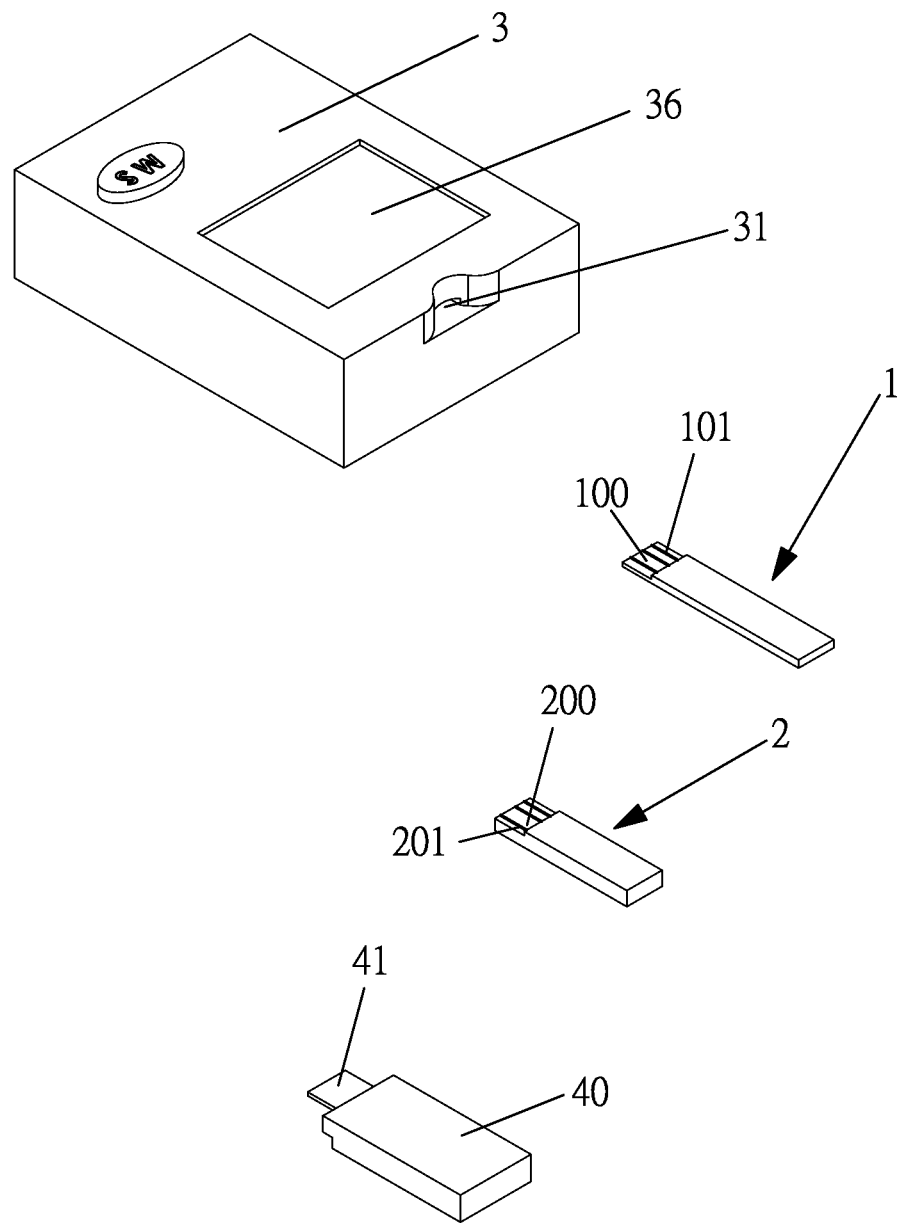
FIG. 5 is a structural top view of an embodiment of the present creation.
Figure 6:
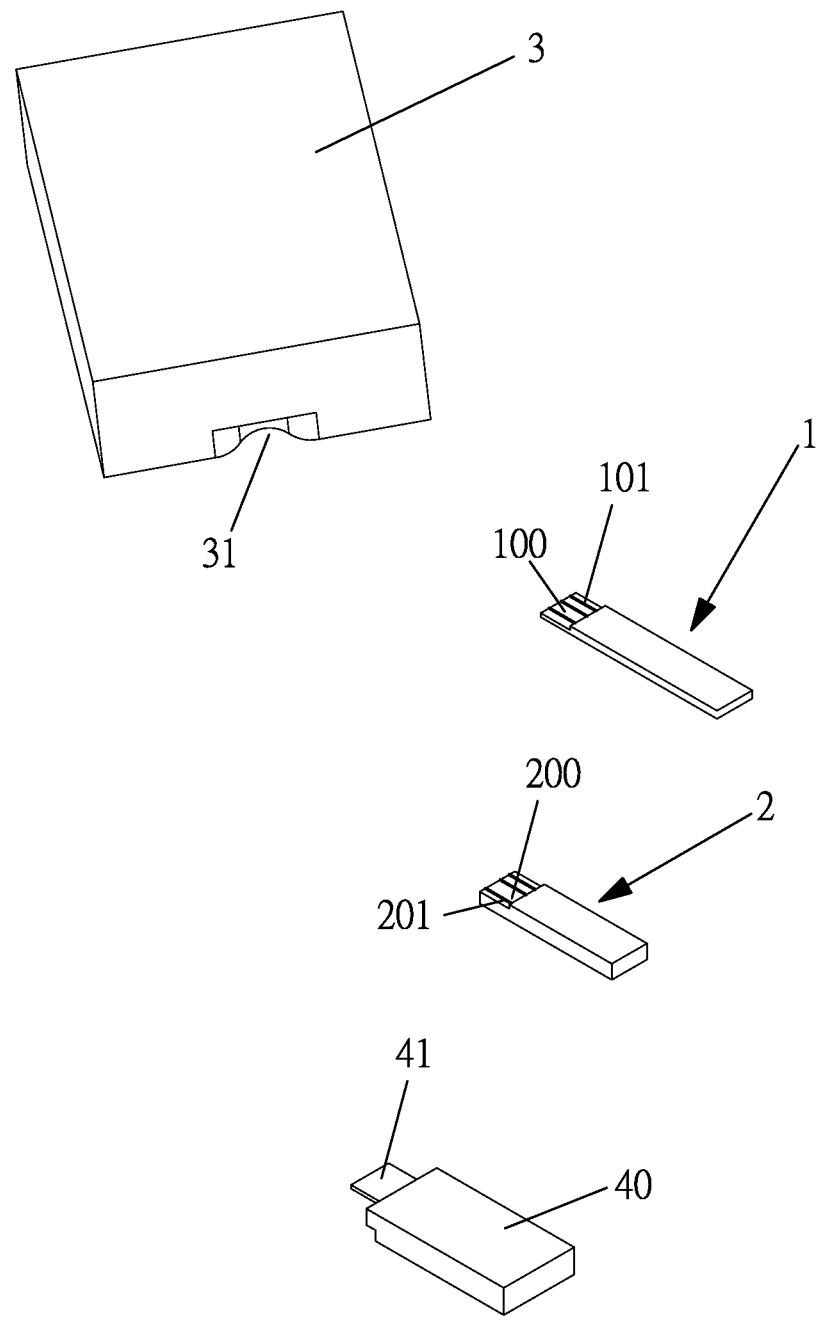
FIG. 6 is a structural bottom view of an embodiment of the present creation.

FIG. 3 and FIG. 4 show another configuration of the wireless signal transmission unit 40 in the present creation, wherein the wireless signal transmission unit 40 is an external electronic apparatus. The wireless signal transmission unit 40 has a transmission connector 41, the transmission connector 41 can be inserted into the detection slot 31 to perform signal transfer, the detection slot inserted apparatus determining unit 32 connected to the detection slot 31 performs recognition and makes a determination on a signal and transfers the signal to a subsequent element for relevant processing, and then a biosignal detection result is transferred via the wireless transmission interface 35 according to a wireless communications protocol.

In the example shown in FIG. 3 and FIG. 4, in the present creation, the wireless signal transmission unit 40 has signal pins different from those of other apparatuses. For example, one slot has 8 pins, wherein pins 2, 3, 6, and 7 serve as signal pins. Alternatively, a different apparatus code is appended to an output signal of the wireless signal transmission unit 40, and when the signal is transferred, the apparatus code of the apparatus is also transferred along with the signal.

Similarly, the electronic device 3 makes a determination according to pins from which the signal is input, and when the wireless signal transmission unit 40 is inserted, it can be determined, according to the mapping table 321 between pins and inserted apparatuses, that the inserted apparatus is the wireless signal transmission unit 40. Alternatively, it is determined, according to the apparatus code identification table 322, that the inserted apparatus is the wireless signal transmission unit 40.

In practice, the user first uses the biosignal detection apparatus 1 to detect a biosignal (for example, heartbeat, blood pressure, blood glucose, body fat, or body temperature), and then inserts the biosignal detection correction unit 2 into the electronic device 3, so as to perform analysis and storage in the electronic device 3. When data obtained through measurement needs to be transferred, the user can connect the wireless signal transmission unit 40 to the electronic device 3, so that data in the storage unit 34 can be transferred via the wireless transmission interface 35 by means of the wireless signal transmission unit 40, for interpretation by a medical institution.

The advantages of the present creation lie in that signals of different types of apparatuses can be transmitted through one detection slot, and the user does not need to make an effort towards determining into which slot a particular apparatus should be inserted, which can improve the user's efficiency and avoid any damage to the device caused by selecting the wrong slot for insertion; additionally, by reducing the number of slots, the size of the device and the number of parts would also decrease, thereby reducing costs.

While the present creation has been described with reference to the embodiments and technical means thereof, various changes and modifications can be made based on the disclosure or teachings described herein. Any equivalent changes made based on the concepts of the present creation, having their effect without departing from the spirit encompassed by the specification and drawings should be construed as falling within the scope of the invention as defined by the appended claims.

According to the aforementioned disclosure, the present creation can surely achieve the expected objectives to provide a wireless biosignal management system, which would have industrial applicability. Thus, the application for a patent is filed according to the law.

| List of Reference Numerals | |
|---|---|
| 1 | Biosignal detection apparatus |
| 2 | Biosignal detection correction unit |
| 3 | Electronic device |
| 31 | Detection slot |
| 32 | Detection slot inserted apparatus determining unit |
| 321 | Mapping table between pins and inserted apparatuses |
| 322 | Apparatus code identification table |
| 33 | Processor |
| 331 | Logic unit |
| 34 | Storage unit |
| 35 | Wireless transmission interface |
| 36 | Display |
| 40 | Wireless signal transmission unit |
| 41 | Transmission connector |
| 42 | Wireless signal slot |
| 100 | Connector |
| 101 | Pin |
| 200 | Connector |
| 201 | Connector pin |

I claim:

1. A biosignal measurement and transmission apparatus having a simplified signal slot, configurable for receiving signals from a biosignal detection apparatus and a biosignal detection correction unit, and performing signal transfer and analysis operations, wherein the biosignal detection apparatus and the biosignal detection correction unit share one detection slot, the measurement and transmission apparatus comprising:
   an electronic device, comprising:
      a housing comprising a single detection slot, the detection slot being used for receiving signals from the biosignal detection apparatus and the biosignal detection correction unit and transferring the received signals to a next-stage apparatus via a wire, wherein a connector of the biosignal detection apparatus and a connector of the biosignal detection correction unit share the detection slot;
the detection slot comprises multiple pins adapted to connect to inserted pins of the biosignal detection apparatus and the biosignal detection correction unit for signal transfer;
wherein the electronic device further comprises:
a detection slot inserted apparatus determining unit, connected to the wire of the detection slot, used for receiving a signal from the detection slot, and capable of identifying a type of an inserted apparatus;
a processor, connected to the detection slot inserted apparatus determining unit and used for receiving a signal from the detection slot inserted apparatus determining unit and performing relevant computation and processing, wherein a logic unit corresponding to the inserted apparatus is mounted in the processor, and the logic unit performs different logic operations depending on types of input signals from different inserted apparatuses; and
a storage unit for storing relevant data, the storage unit having memory blocks that correspond to different inserted apparatuses, so as to separately store measurement information of the different inserted apparatuses, for subsequent display, management and use.

2. The biosignal measurement and transmission apparatus having a simplified signal slot according to claim 1, wherein the biosignal detection apparatus is used for detecting at least one biosignal of a user, the biosignal detection apparatus comprises a connector for transmitting a signal, and the connector comprises multiple pins for signal transfer; the biosignal detection correction unit provides data of a reference group to the storage unit to assist in detection of the biosignal, and the biosignal detection correction unit has a connector that comprises multiple pins for signal transfer.

3. The biosignal measurement and transmission apparatus having a simplified signal slot according to claim 1, wherein the biosignal is one of heartbeat, blood pressure, blood glucose, body fat, and body temperature.

4. The biosignal measurement and transmission apparatus having a simplified signal slot according to claim 1, wherein the biosignal detection apparatus and the biosignal detection correction unit have different signal pins, and different biosignal detection apparatuses have different pins for signal transfer;
wherein the detection slot inserted apparatus determining unit identifies an inserted apparatus by making a determination according to pins from which the signal is input, automatically interpreting differences between pins of different apparatuses, and determining transmission input pins of the signal, wherein a mapping table between pins and inserted apparatuses is stored in the detection slot inserted apparatus determining unit, and the mapping table defines a correspondence between a signal output pin of each apparatus inserted into the detection slot and the apparatus, so that the detection slot inserted apparatus determining unit searches, according to a signal pin of an inserted apparatus, for the corresponding apparatus in the table, determines a type of the signal from the inserted apparatus, and transmits the signal to a next-stage apparatus for subsequent processing.

5. The biosignal measurement and transmission apparatus having a simplified signal slot according to claim 4, wherein output signals of the biosignal detection apparatus and the biosignal detection correction unit comprises different apparatus codes, and apparatus codes transferred in signals of different biosignal detection apparatuses are also different;
wherein the detection slot inserted apparatus determining unit identifies an inserted apparatus by making a determination according to the apparatus code, determining differences between apparatuses according to different apparatus codes, and determining the position from which the signal is transmitted, wherein an apparatus code identification table is stored in the detection slot inserted apparatus determining unit, and the mapping table defines a correspondence between an apparatus code in an output signal of each apparatus inserted into the detection slot and the apparatus, so that the detection slot inserted apparatus determining unit searches, according to the apparatus code of an inserted apparatus, for the corresponding apparatus in the table, and thus can determine the type of the signal of the inserted apparatus according to the correspondence between identification codes and inserted apparatuses, and transfers the signal to a next-stage apparatus for subsequent processing.

6. The biosignal measurement and transmission apparatus having a simplified signal slot according to claim 1, further comprising:
a display disposed in the electronic device, connected to the storage unit, and used for displaying relevant measurement information.

7. The biosignal measurement and transmission apparatus having a simplified signal slot according to claim 1, further comprising:
a wireless transmission interface, connecting with the processor and the storage unit, and used for modulating a signal from the processor into a wireless signal for transfer, or used for demodulating a wireless signal into a baseband signal for signal processing by the processor; and
a wireless signal transmission unit, connected to the wireless transmission interface, the wireless signal transmission unit being mounted in the electronic device to receive a biosignal detection result and transmit the detection result according to a wireless communications protocol.

8. The biosignal measurement and transmission apparatus having a simplified signal slot according to claim 7, wherein the wireless signal transmission unit is a Bluetooth transmission unit.

9. The biosignal measurement and transmission apparatus having a simplified signal slot according to claim 1, further comprising:
a wireless transmission interface, connecting with the processor and the storage unit, and used for modulating a signal from the processor into a wireless signal for transfer, or used for demodulating a wireless signal into a baseband signal for signal processing by the processor; and
a wireless signal transmission unit, being an external electronic apparatus, wherein the wireless signal transmission unit has a transmission connector, the transmission connector can be inserted into the detection slot to perform signal transfer, the detection slot inserted apparatus determining unit connected to the detection slot performs recognition and makes a determination on a signal and transfers the signal to a subsequent element for relevant processing, and then a biosignal detection result is transferred via the wireless transmission interface according to a wireless communications protocol.

10. The biosignal measurement and transmission apparatus having a simplified signal slot according to claim 9, wherein the wireless signal transmission unit has signal pins different from those of other apparatuses, the electronic device makes a determination according to pins from which a signal is input, and when the wireless signal transmission unit is inserted, it can be determined, according to a mapping table between the signal pins of the wireless signal transmission unit and inserted apparatuses, that the inserted apparatus is the wireless signal transmission unit.

11. The biosignal measurement and transmission apparatus having a simplified signal slot according to claim 9, wherein a different apparatus code is appended to an output signal of the wireless signal transmission unit, and when the signal is transferred, the apparatus code of the inserted apparatus is also transferred along with the signal, so that the electronic device can determine, according to an apparatus code identification table, that the inserted apparatus is the wireless signal transmission unit.

12. The biosignal measurement and transmission apparatus having a simplified signal slot according to claim 9, wherein the wireless signal transmission unit is a Bluetooth transmission unit.

* * * * *